United States Patent [19]
Weldon

[11] Patent Number: 5,195,990
[45] Date of Patent: Mar. 23, 1993

[54] CORONARY CATHETER

[75] Inventor: Thomas D. Weldon, Aquadilla, P.R.

[73] Assignee: Novoste Corporation, Aquadilla, P.R.

[21] Appl. No.: 757,684

[22] Filed: Sep. 11, 1991

[51] Int. Cl.$^5$ .......................................... A61M 25/00
[52] U.S. Cl. .................................. 604/281; 604/264; 604/280
[58] Field of Search ........................ 128/657, 658, 654; 604/280–284, 53, 264

[56] References Cited

U.S. PATENT DOCUMENTS

| 3,419,010 | 12/1968 | Williamson . | |
|---|---|---|---|
| 3,726,269 | 4/1973 | Webster, Jr. | 128/2.05 F |
| 3,935,857 | 2/1976 | Co | 128/2.05 |
| 3,938,501 | 2/1976 | Erikson | 128/2 A |
| 4,033,331 | 7/1977 | Guss et al. | 128/2 M |
| 4,117,836 | 10/1978 | Erikson | 128/2.05 R |
| 4,169,464 | 10/1979 | Obrez | 128/657 |
| 4,279,252 | 7/1981 | Martin | 128/349 R |
| 4,292,976 | 10/1981 | Banka | 128/656 |
| 4,385,635 | 5/1983 | Ruiz | 128/658 |
| 4,563,338 | 2/1986 | Todd | 604/281 |
| 4,568,181 | 1/1986 | Wijayarathra et al. | 604/280 |
| 4,747,840 | 5/1988 | Ladika | 604/281 |
| 4,882,777 | 11/1989 | Narula | 604/281 |
| 4,883,058 | 11/1989 | Ruiz | 128/654 |
| 4,973,306 | 11/1990 | Ruiz | 604/53 |
| 5,016,640 | 5/1991 | Ruiz | 128/658 |

FOREIGN PATENT DOCUMENTS 903636 6/1973 Canada .

OTHER PUBLICATIONS

Mechanics of Selective Coronary Artery Catheterization Via Femoral Approach, K. Amplatz, et al., Radiology 89:1040–1047 (1967).

An Improved Technique For Right Coronary Artery Catheterization, R. White, et al., Am. J. of Roentgenology, Radium Therapy and Nuclear Medicine vol. 113, pp. 562–566, (1971).

Nonoperative Dilation of Coronary-Artery Stenosis, A. R. Gruenzing, et al., N. Engl. J. Med. 301:61 (1979).

Anatomy of the Coronary Arteries, T. N. James, Harper and Row, New York pp. 38–41 (1961).

Congenital Anomalies of the Coronary Arteries, J. A. Ogden, Am. J. Cardiol. 25:474, (1970).

Coronary Arteriography by the Single Catheter Percutaneous Femoral Technique, F. W. Schoonmaker, et al., Circulation, 50:735, (1974).

Anomalous Origin of the Left Circumflex Coronary Artery, H. L. Page, et al., Circulation, 50:768, (1974).

Clinical Angiographic and Hemodynamic Findings in Patients with Anomalous Origins of the Coronary Arteries, B. R. Chaitman, et al. Circulation, 53:122 (1976).

Complications Associated with Cardiac Catheterization and Angiography, J. W. Kennedy, et al., Cather. Cardiovase, Diagn. 8:5, (1982).

Transfemoral Selective Bilateral Pulmonary Arteriography with a Pulmonary Artery Seeking Catheter, J. H. Grollman, Radiology, 96:202, (1970).

Selective Coronary Arteriography by the Percutaneous Femoral Artery Approach, Martial G. Bourassa, M.D., et al., The American Journal of Roentgeniogy, Radium Therapy and Nuclear Medicine vol. 107, No. 1, Oct., (1969).

Preshaped Polyethylene Catheters For Percutaneous Hemodynamic and Angiographic Studies, Martial G. Bourassa, M.D., Angiology, vol. 22, No. 6; 320–331, Jun., (1991).

(List continued on next page.)

Primary Examiner—C. Fred Rosenbaum
Assistant Examiner—Manuel Mendez
Attorney, Agent, or Firm—Kenyon & Kenyon

[57] ABSTRACT

The coronary catheter of the present invention has an elongated tubular member or shaft, with a proximal end portion and the distal end portion. The distal end portion terminates in a tip end portion. In accordance with the present invention, the distal end portion of the catheter is curved in three dimensions and cooperative with the shape of the human aortic arch so as to automatically place the tip end of the catheter into proximity with the right coronary ostium as the distal end portion passes over the aortic arch and into the ascending aorta.

8 Claims, 6 Drawing Sheets

OTHER PUBLICATIONS

Selective Coronary Angiography Using A Percutaneous Femoral Technique, Bourassa, et al., Canadian Medical Ass'n Journal, 102:170–173 (1970).

Selective Coronary Arteriography: A Percutaneous Transfemoral Technic., M. P. Judkins, Radiology 89:815–824 (1967).

Percutaneous Transfemoral Selective Coronary Arteriography, M. P. Judkins, Radiol. Clin. North Am. 6:467–492 (Dec., 1968).

Safety Guidespring for Percutaneous Cardiovascular Catheterization, C. T. Dotter, et al., Am. J. Roentgenol. 98:975–980 (Dec., 1966).

Teflon-coated Safety Guides: An Adjunct to the Use of Polyurethane Catheters, M. P. Judkins, Am. J. Roentgenol, 104:223, (Sep., 1968).

Coronary Artery Surgery Study, Principal Investigators of CASS and Their Associates: National Heart, Lung, and Blood Institute Coronary Artery Surgery Study (CASS), Circulation, 63(suppl 1):1-1 to 1-81, (Jun., 1981).

Prevention of Complications of Coronary Arteriography, M. P. Judkins, Circulation, 49(4):599–602, (Apr., 1974) (editorial).

Lumen-following Safety-J Guide for Catheterization of Tortuous Vessels, M. P. Judkins, et al., Radiology, 88:1127–1130, (Jun., 1967).

Optimal Resources for Examination of the Heart and Lungs: Cardiac Catheterization and Radiographic Facilities, G. C. Friesinger, et al., Circulation, 68:891A–920A, (Oct., 1983).

Guiding Catheter Selection for Right Coronary Artery Angioplasty, Richard K. Myler, M.D., et al., Catheterization and Cardiovascular Diagnosis 19:58–67 (1990).

Double Loop Guiding Catheter: A Primary Catheter for Angioplasty of the Right Coronary Artery; Djavad T. Arani, M.D., et al. Catheterization and Cardiovascular Diagnosis 15:125–131 (1988).

A New Catheter for Angioplasty of the Right Coronary Artery and Aorto-Coronary Bypass Grafts, Djavad T. Arnani, M.D., Catheterization and Cardiovascular Diagnosis 11:647–653 (1985).

Right Coronary Artery Dissection—A Complication of Cardiac Catheterization and Coronary Angiography, Behrooz Eshaghy, M.D., et al., pp. 551–553 Chest, 70:4, Oct., 1976.

Isolated Obstruction of the Right Coronary Artery, A. Bakst, M.S., et al. pp. 18–74 Chest, vol. 65, 1, Jan. (1974).

USCI POSITROL II ® & NYCORE TM Cardiovascular Catheters, USCI Cardiology & Radiology Products, Dec. 1980/5070434 (Division of C. R. Bard, Inc.).

The Small Right Coronary Artery: Angiographic Implications-Case Reports, Venkataraman, et al. pp. 53–57 Angiology, The Journal of Vascular Diseases, vol. 39, Jan., 1988.

Right Coronary Arteriography in Dogs, Sahler, et al., pp. 311–315, VM/SAC, Mar., 1984, vol. 79, No. 3.

Introducing: A New Ducor ® Brachial-Coronary Angiographic Catheter, Cordis, 1973.

*Coronary Arteriography and Angioplasty*, Spencer B. King, III M.D., John S. Douglas, Jr. M.D., Chapter 7, "Coronary Artery and Left Ventriculography: Judkins Technique", pp. 182–238 (1985).

Bourassa Cardiovascular Catheters brochure published by USCI, a division of C. R. Bard, Inc., Rev. Jun. 1972.

FIG. 3b  TOP VIEW

FIG. 3c  END VIEW

FIG. 3a  SIDE VIEW

CORONARY CATHETER

BACKGROUND OF THE INVENTION

The present invention relates in general to catheters useful in the diagnosis and/or treatment of coronary diseases or conditions. More specifically, the present invention relates to coronary catheters for use in the diagnosis and/or treatment of diseases or conditions in the right coronary artery.

Diagnosis and/or treatment of coronary artery diseases or conditions typically involves the insertion of a catheter through the vascular system of a patient and to the proximity of the site which is being treated or examined. For example, in coronary angiography or arteriography, a hollow catheter is typically inserted into an artery, such as the femoral artery in the patient's leg, and guided by a guide wire or guiding catheter upwardly through the descending aorta, over the aortic arch and downwardly into the ascending aorta. The tip of the catheter is then inserted into the ostium of either the right or the left coronary artery, depending on which specific artery is to be examined. After the tip of the catheter is inserted into the ostium, radiopaque liquid is injected through the catheter to provide an x-ray image of the condition of the particular artery and thus aid in the diagnosis of any coronary artery condition or disease present.

Development of a catheter for use in the diagnosis and/or treatment of coronary diseases or conditions involves application of various and sometimes competing considerations. There are, for example, physiological considerations in the design of coronary catheters. The openings into the left and right coronary arteries are not symmetrical. If the ascending aorta is viewed in cross-section and from below, the ostium for the right coronary artery is located generally at an eleven o'clock position and the ostium for the left coronary artery is located at approximately the three o'clock position. Because of this asymmetry, catheters have been designed with different tip shapes peculiar to whether the procedure is to be carried out for the right or left coronary arteries. Dr. Melvin Judkins described particular catheter tip configurations for right and left artery procedures many years ago. Catheters having such tip configurations are commonly referred to as "Judkins" catheters.

Because of the central (three o'clock) position of the ostium for the left coronary artery, the so-called "left" Judkins catheter works well, and requires relatively little manipulation by the physician to place the tip end of the catheter into the coronary ostium. The ostium for the right coronary artery, however, is not located in as convenient a position, and the Judkins catheter for the right coronary artery requires that the doctor to rotate the catheter approximately 180° after it is inserted past the ostium and then to withdraw the catheter slightly until the tip enters the right ostium. In a living patient, where the heart is beating and the artery pulsing, placement of the right Judkins catheter can be very difficult, and may require extensive experience before a level of proficiency is attained.

To provide sufficient rigidity for rotation of the catheter to the desired position, right coronary artery catheters typically have a metal braid within the wall of the catheter. The metal braid stiffens the catheter and transmits the torque exerted by the physician when the physician twists the proximal end of the catheter, which is located outside the patient, to rotate the distal end that is located in the ascending aorta.

The drawback with the braided catheter, however, is that the braid results in a catheter having a larger outside diameter. Because doctors prefer the inside diameter of the catheter to be as large as possible for the maximum flow rate of radiopaque liquid (so as to provide the sharpest x-ray image) the provision of a metal braid in the wall of a catheter is typically accommodated by increasing the outside diameter of the catheter.

The larger outside diameter, however, requires a larger incision for entry of the catheter into the patient's artery. Larger incisions, however, require longer times to clot. Increased clotting time may require an overnight stay of the patient in the hospital, resulting in increased cost as compared to procedures carried out on an out-patient basis.

As a result of these competing considerations, there continues to be a need and desire for improved coronary catheters. In particular, there is a continuing need for coronary catheters for diagnosis and treatment of the right coronary artery, which catheters may be readily placed into the right coronary artery ostium but also have minimum wall thickness, thereby allowing for the maximum inside diameter for radiopaque fluid flow and the smallest outside diameter for the minimum incision.

One attempt to provide an alternative coronary catheter for use with the right coronary artery is disclosed in U.S. Pat. No. 4,883,058 to Ruiz. In the Ruiz patent, the distal end of the catheter comprises a relatively sharp curve with a small radius of curvature at the most distal tip portion and a larger curve in the opposite direction upstream of the tip portion. The curvature of the larger curve is not as great as the curvature of the aortic arch, so as to bias the tip portion against the outer wall of the ascending aorta.

Although the '058 Ruiz patent may be a step in the right direction, it also appears to have several shortcomings. Because the tip is biased outwardly, the guidewire must remain in the catheter as it passes upwardly along the descending aorta and over the aortic arch and into the ascending aorta. Otherwise the tip may become caught in the arterial branches in the top of the aortic arch. If the guidewire must remain in the catheter, the catheter cannot be periodically flushed with radiopaque liquid as physicians often desire to do to visualize the location of the catheter tip as it moves through the aorta. The catheter shown in the '058 Ruiz patent also requires the physician to apply a torque to the proximal end of the catheter to cause the catheter tip to rotate somewhat for insertion into the ostium.

Accordingly, it is an object of the present invention to provide a catheter for use unconnected with the right coronary artery which does not suffer from the drawbacks described above.

It is a more specific object of the present invention to provide a catheter for the diagnosis and treatment of diseases or conditions of the right coronary artery which requires minimum manual adjustment or positioning for placement of the tip of the catheter in the right ostium.

It is yet a further object of the present invention to provide a catheter for the right coronary artery which cooperates with the shape of human aortic arch for automatic placement of the catheter tip in the proximity of ostium so that minimum adjustment or manipulation of the catheter is required.

SUMMARY OF THE INVENTION

The present invention is embodied in a coronary catheter having an elongated tubular member or shaft, with a proximal end portion and the distal end portion. The distal end portion terminates in a tip end portion. In accordance with the present invention, the distal end portion of the catheter is curved in three dimensions and cooperative with the shape of the human aortic arch so as to automatically place the tip end of the catheter into proximity with the right coronary ostium as the distal end portion passes over the aortic arch and into the ascending aorta.

The coronary catheter of the present invention may comprise of a plurality of curves of increasingly smaller radii in the direction of the tip end portion, and each of said curves preferably lies in a different plane. The result is preferably a generally spiral-like in shape and, more particularly, when viewed from a lateral direction, the distal end portion comprises a most distal portion which is curved and lies substantially within a first plane and a more proximal portion which is curved and lies substantially within a second plane, the second plane being disposed at an angle to said first plane. The coronary catheter may further include an arcuate portion not lying in either of the aforesaid planes, but extending between and connecting the most distal end portion and the more proximate portions.

In accordance with another aspect of the present invention, the distal end includes a portion between two areas of smaller radii which is deformed slightly during passage over the aortic arch, so as to bias the tip end portion of the catheter for entry into the right coronary ostium.

DESCRIPTION OF THE PREFERRED EMBODIMENT

Figures 1, 2:
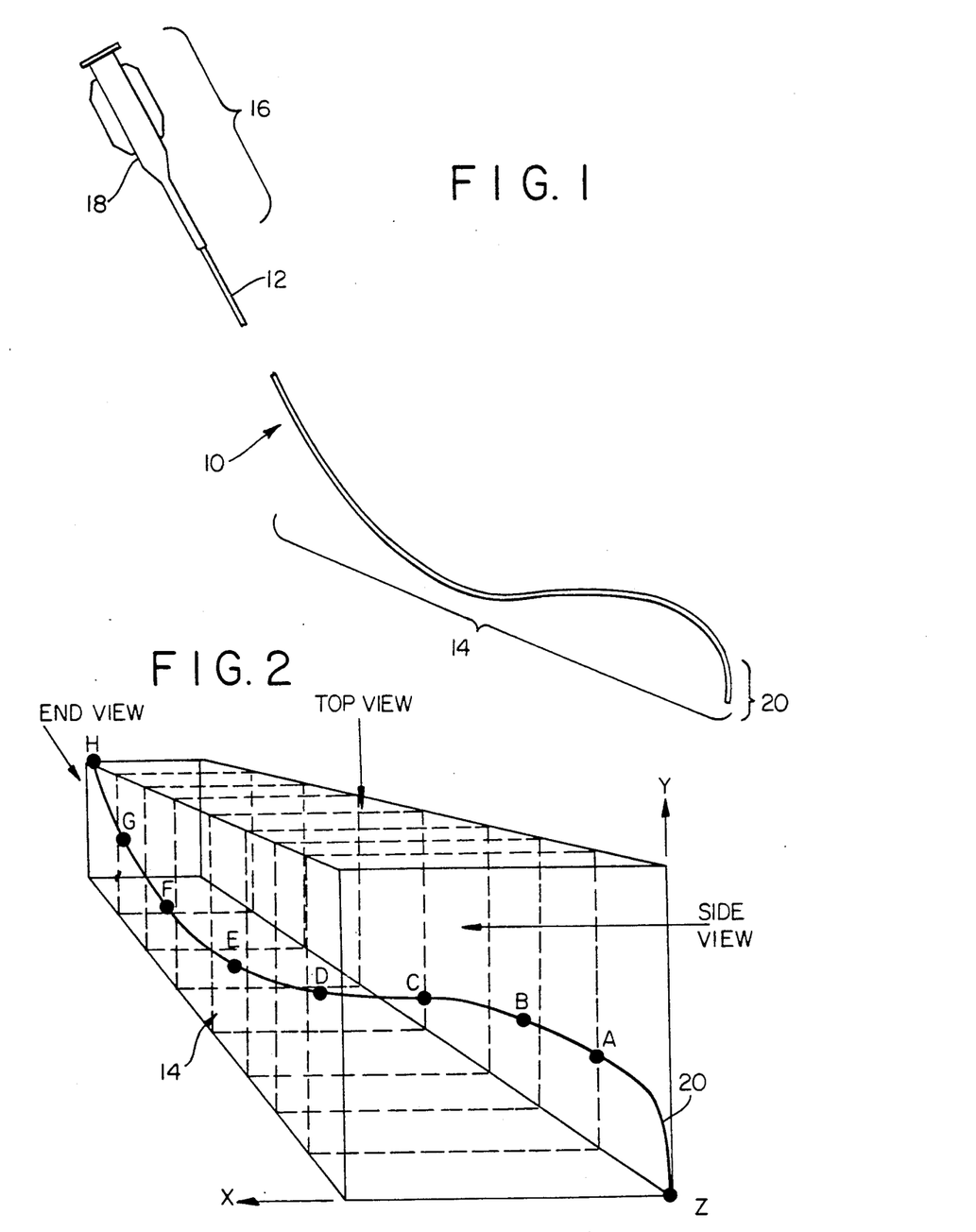
FIG. 1 is a perspective view of a catheter embodying the present invention.
FIG. 2 is an enlarged perspective view of the forming wire used to form the particular tip shape of the present invention on the catheter shown in FIG. 1.

The present invention is generally embodied in a catheter 10 of the type typically used for angioplasty or angiographic procedures. The catheter 10 includes a hollow elongated extruded tube or shaft 12, which extends from a distal end portion 14 to a proximal end portion 16. A lumen extends throughout the length of the tube for passage of radiopaque dye and the like, and communicates at the proximal end, with a hub 18 for attachment of syringes and the like. The material of the catheter tube may be of any suitable plastic material, as is well-known in the medical field. Most preferably, the catheter is made of nylon, in accordance with the solid state polymerization procedure described in U.S. Pat. No. 4,963,306, incorporated by reference, wherein the body or shaft portion of the catheter is subjected to solid state polymerization, and solid state polymerization is inhibited in the distal end portion 14 to provide a softer and more pliable distal end.

The distal end 14 terminates in the very tip portion 20 of the catheter, which enters the ostium. The tip end 20 preferably is made softer than the rest of the distal end portion 14, utilizing the softening process set forth in copending application, U.S. Ser. No. 07/703,486 filed May 21, 1991, which is hereby incorporated-by reference.

In accordance with the present invention, the distal end portion 14 of the catheter 10 defines a relatively complex, three-dimensional shape which cooperates with the normal shape of the human aorta in order to automatically place the tip end 20 into the ostium of the right coronary artery 30 with minimum manual adjustment. The particular shape is formed on the distal end portion 14 of the catheter by first inserting the distal end over a forming wire of the desired shape. The distal end portion 14 of the catheter 10 is then immersed in boiling water for two to three minutes to set the shape of the distal end of the catheter to conform to that of the forming wire. After the catheter has cooled, and the forming wire removed, the shape of the distal end of the catheter corresponds essentially to the shape of the forming wire. Accordingly, when the shape of the forming wire is discussed hereinafter it will be understood that the shape of the distal end of the resulting catheter corresponds to the shape of the forming wire.

The shape of the forming wire for forming the catheter of the present invention may be seen in FIG. 2, which is superimposed on three dimensional, x, y and z axes. The following chart defines the location of the points 0 through H the forming wire relative to the x, y and z axes. For example, the very tip end of the forming wire is designated point "0" and the x, y and z positions are respectively 0, 0 and 0. Point "A" on the forming wire is located at a position corresponding to the position 0 inches along the x axis, one inch along the z axis and 0.85 inches along the y axis. By comparing the points along the forming wire to the chart below, the three dimensional shape of the present catheter may be visualized.

| POINT | x | y | z |
|---|---|---|---|
| 0 | 0.00 | 0.00 | 0.00 |
| A | 0.00 | 0.85 | 1.00 |
| B | 0.05 | 0.90 | 2.00 |
| C | 0.30 | 0.70 | 3.00 |
| D | 0.85 | 0.60 | 4.00 |
| E | 1.80 | 0.80 | 5.00 |
| F | 2.80 | 1.15 | 6.00 |
| G | 3.80 | 1.80 | 7.00 |
| H | 4.80 | 2.80 | 8.00 |

Figure 3A:
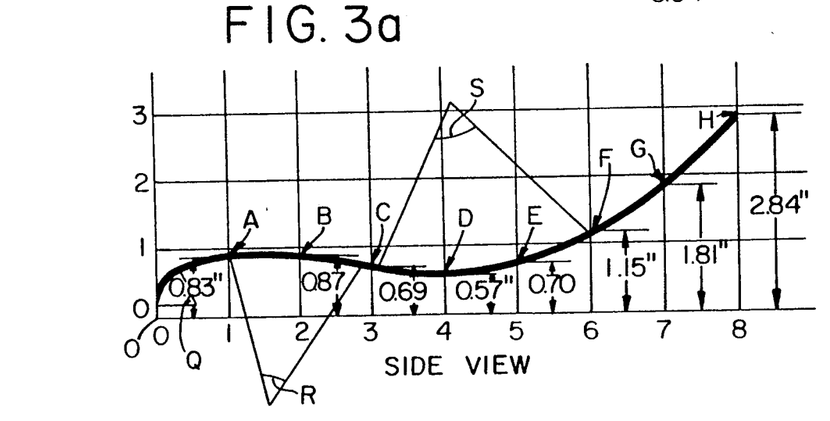
FIGS. 3a-c respectively, are side, top and end views of the tip forming wire shown in FIG. 2.
Figure 3B:
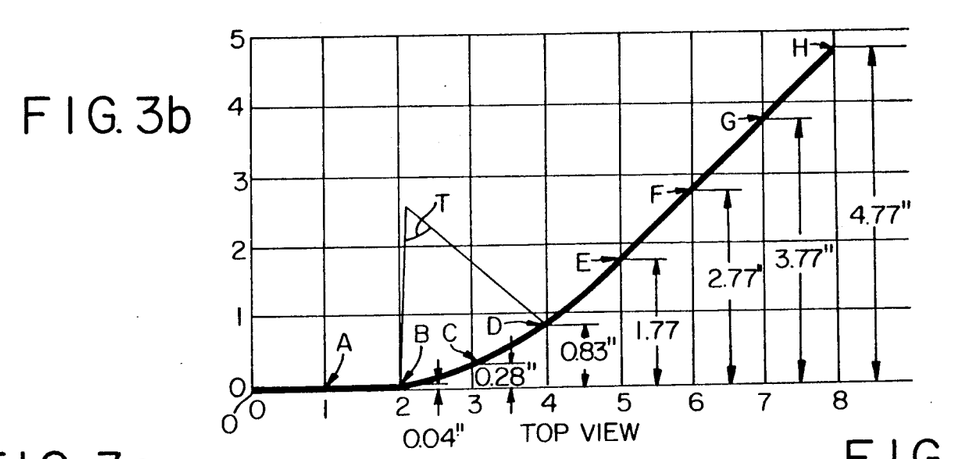
Figure 3C:
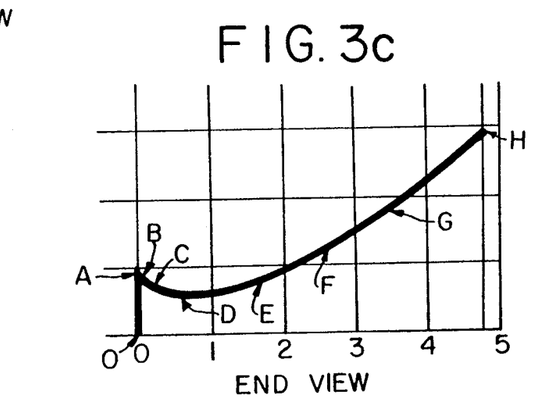

Alternatively, the forming wire may be viewed as depicted in FIGS. 3a-c. FIG. 3a is a side view of the forming wire. The tip end portion of the catheter corresponds the left hand most end of the forming wire, and the shaft 10 of the catheter would extend from the right end of the forming wire as shown in FIG. 3a. FIG. 3b is a top view, looking down on the forming wire of FIG. 3a and FIG. 3c is an end view of the forming wire as viewed from the right hand side of FIG. 3a.

As may be seen in FIG. 3a, the catheter comprises, at the tip end portion, a relatively sharp curve defined along arc "Q", which extends approximately between points "0" and "A". In the side view, the distal end portion also includes a more gradual curve along arc R approximately extending between points "A" and "C", and another curve defined along arc S, extending approximately between points "C" and "F". From the side view a final and yet more gradual curve extends between points "F" and "H".

When the forming wire is viewed from the top, as shown in FIG. 3b, it may be seen that the most distal end of the forming wire located generally between points "0" and "B", which includes arc Q and at least a portion of arc R, lies in one plane, and at least a portion of arc S lies in another plane. These two planes are connected by a curved portion, generally designated arc T in the top view.

FIG. 3c is an end view of the forming wire, as viewed from the proximal end of the forming wire.

It may be seen from the above that the shape of the forming wire is a relatively complex three-dimensional shape, which overall is very generally spiral-like. As noted above, when the catheter is heat formed over the forming wire, it corresponds essentially to the shape of the forming wire, and the discussion above relative to the shape and configuration of the forming wire applies equally to shape and configuration of the distal end of the formed catheter.

Figure 4:
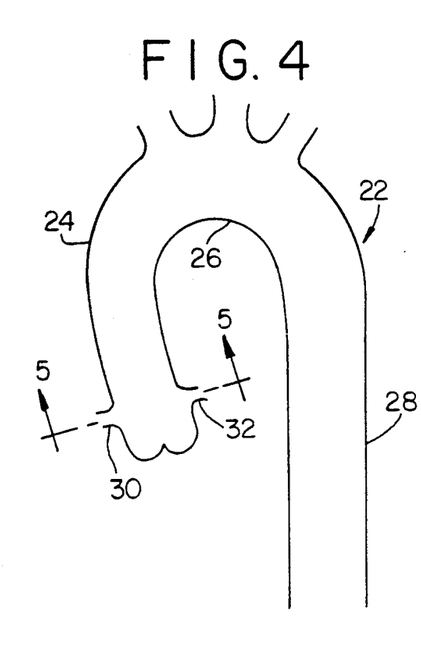
FIG. 4 is a partial diagrammatic view of the ascending aorta, aortic arch and descending aorta in the typical human.
Figure 5:
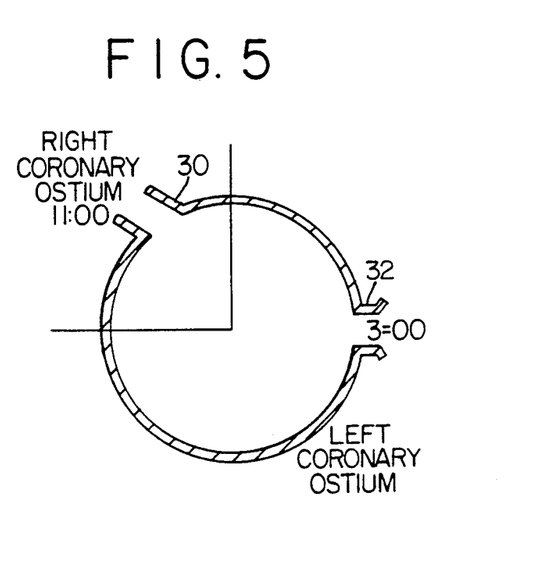
FIG. 5 is a sectional view of the ascending aorta, taken along line 5—5 of FIG. 4.

Referring now to FIG. 4, FIG. 4 is a generally diagrammatic view of a aorta 22, including the ascending aorta 24, aortic arch 26, and descending aorta 28. As apparent from FIG. 4, the aortic arch is roughly shaped like the handle of a cane, extending upwardly from the descending aorta 28 over the heart and downwardly into the ascending aorta 24. The right and left coronary arteries branch outwardly from the lower end of the ascending aorta 24. When viewed in cross-section in FIG. 5, looking upwardly into the ascending aorta 24, and picturing the face of a clock on the ascending aorta 24, it may be seen that the ostium 30 for the right coronary artery is generally at the eleven o'clock position. The ostium 32 for the left coronary artery is at the three o'clock position.

Figure 6A:
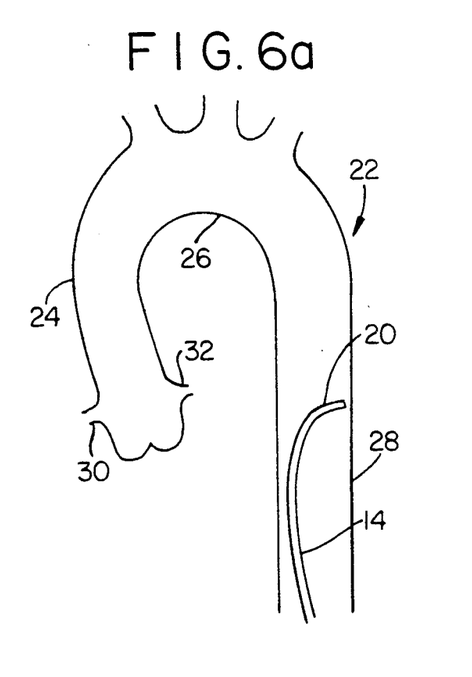
FIGS. 6a-g are diagrammatic views of the human aorta, as shown in FIG. 4, depicting the catheter of the present invention in progressively advanced positions as it is inserted into the right coronary ostium.
Figure 6B:
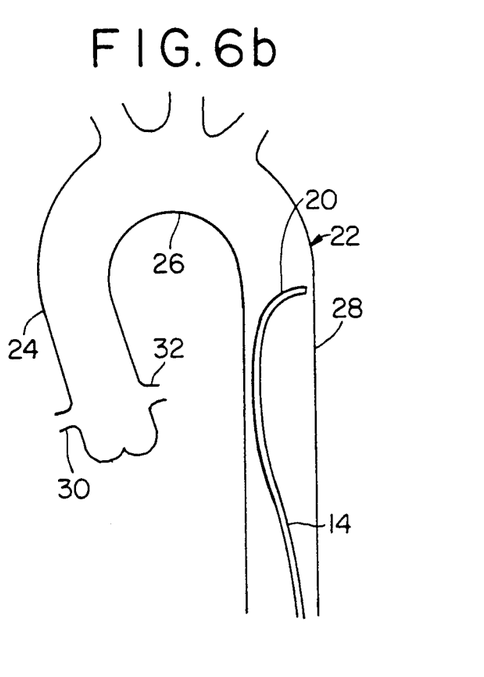
Figure 6C:
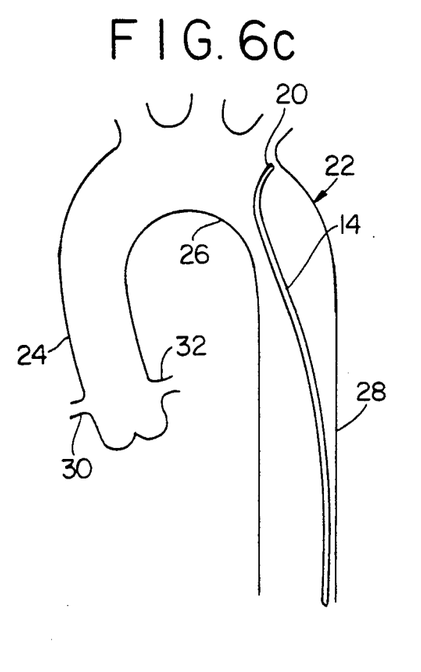
Figure 6D:
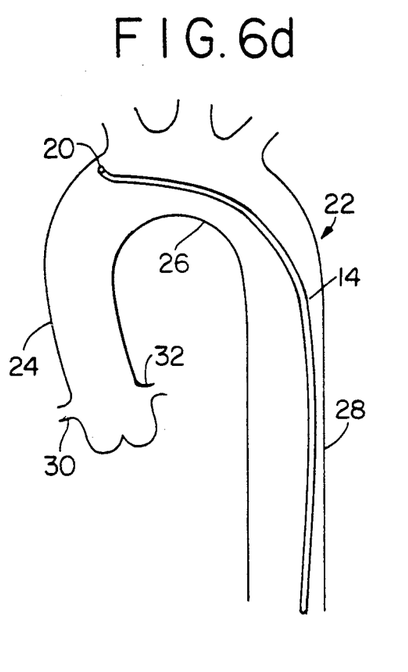
Figure 6E:
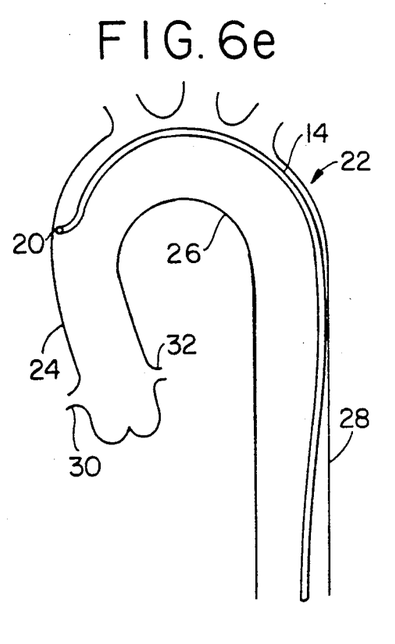
Figure 6F:
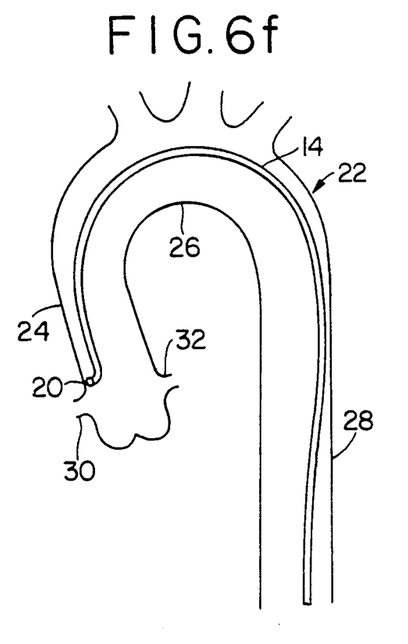
Figure 6G:
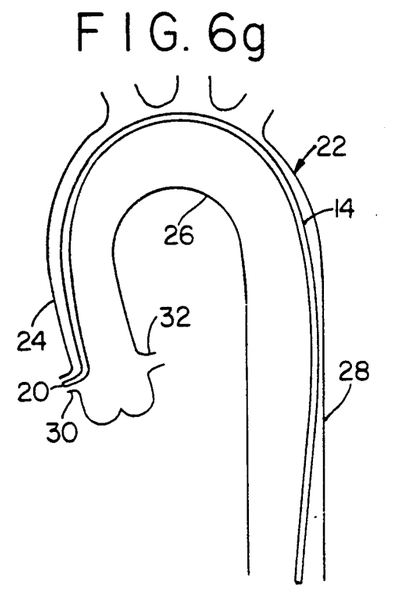

The operation of inserting the catheter 10 of the present invention into the ostium 30 for the right coronary artery is best depicted in FIGS. 6a-g. FIG. 6a shows the catheter 10 correctly positioned in the aorta 22. As shown in FIG. 6b, the catheter in the present invention is advanced upwardly, through the descending aorta 28 and into the vicinity of the aortic arch 26. The catheter 10 may be advanced to this location over a guidewire or through a guiding catheter. At approximately this location or earlier, the guidewire or guiding catheter may be removed to permit the distal end 14 of the catheter 10 to assume its unique shape for further advancement of the catheter toward and over the aortic arch 26. As the catheter 10 approaches the aortic arch 26, the tip end portion 20 generally is adjacent to the outer wall of the aorta 22, and a more proximal portion of the distal end 14 rests generally against the inner wall of the aorta 22 (as best seen in FIG. 6b). As the catheter 10 moves upwardly, the shape of the distal end 14 of the catheter cooperates with the walls of the aorta 22 to turn the distal end in a clockwise direction (as viewed from the proximal end) as the tip end 20 moves toward the ascending aorta 24 (see FIG. 6c). As the tip end of the catheter moves over the aortic arch 26, the tip end 20 of the catheter continues to cooperate with the outer wall of the aortic arch 26 and the more proximal portion of the distal portion 14 bends over the aortic arch 26 (FIG. 6d). As the tip end portion 20 moves downwardly into the ascending aorta 24, the more proximal portion of the distal end 14 contacts the outer wall of the descending aorta 28 and bends over the aortic arch 26, continuing to turn the tip end portion toward a position for automatic insertion into the right coronary ostium 30 (FIG. 6e). FIG. 6f shows a more advanced position of the catheter 10. At this position, the portion of the catheter generally between points 2 and 4 places an upward spring pressure on the tip end portion 20 as it advances toward the aorta right coronary ostium 30. The portion of the catheter substantially between points 5 and 8 comprises a back bend which extends over the aortic arch 26 as the tip end portion advances into the proximity of the aortic arch 26. As the catheter 10 is advanced further (FIG. 6g), the tip end portion 20 continues to move downwardly, rotating slightly clockwise to a position ready for direct entry into the right coronary ostium 30 when it is reached. Upon reaching the right coronary ostium 30, the spring pressure exerted by the portion between points 2 and 4 automatically inserts the tip end portion 20 into the right coronary ostium 30 with little adjusting required.

If the catheter 10 is not inserted precisely in the manner described above, the particular shape of the tip end 20 cooperates with the aorta 22 to adjust the position of the tip end to compensate for the initial mis-positioning of the catheter 10. For example, if the distal end 14 of the catheter is slightly counter-clockwise, the tip moves over the aortic arch 22 and promptly is moved into a position for ready entry into the right coronary ostium 30. If the tip 20 is over rotated in a clockwise position, the relative curvature of the distal end and the aortic arch 26 causes the distal end to flip completely over, again positioning the tip portion 20 of the catheter 10 for ready entry into the right coronary ostium 30. Thus, the catheter 10 readily compensates for physician errors or mistakes in the proper placement of the catheter 10.

Figure 7A:
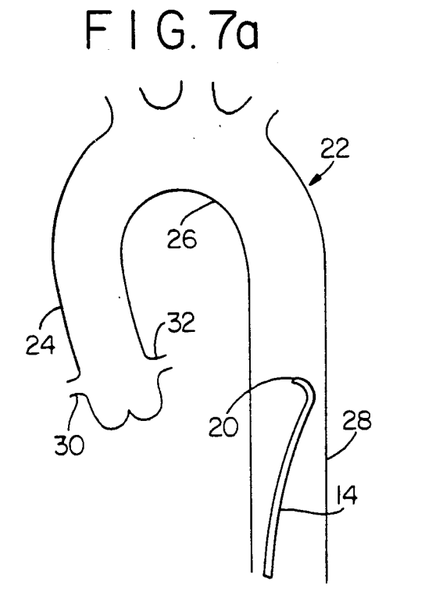
FIGS. 7a-g are diagrammatic views of the human aorta, as shown in FIG. 4, depicting the catheter of the present invention in progressively advanced positions after the catheter has been inserted in a mis-aligned position.
Figure 7B:
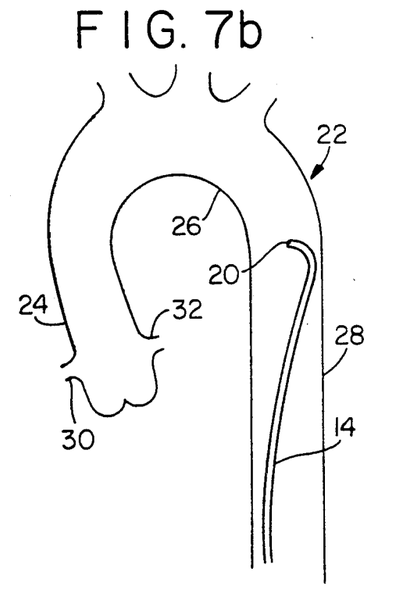
Figure 7C:
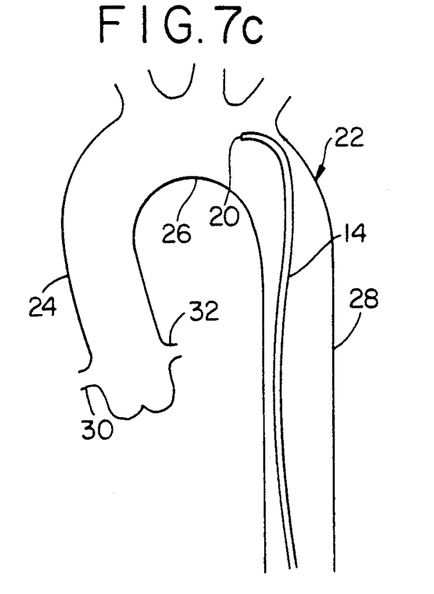
Figure 7D:
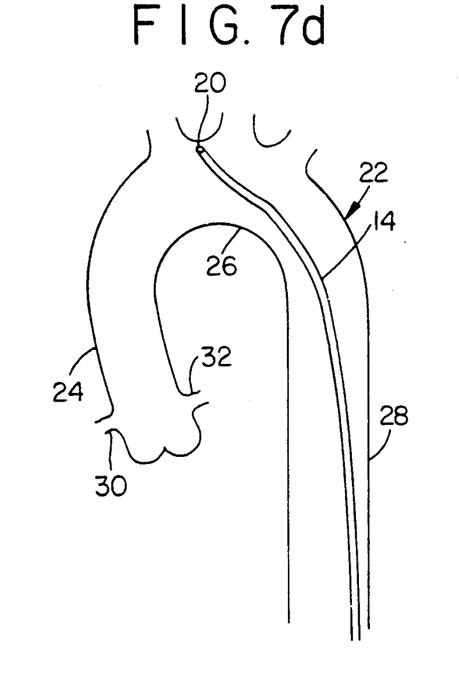
Figure 7E:
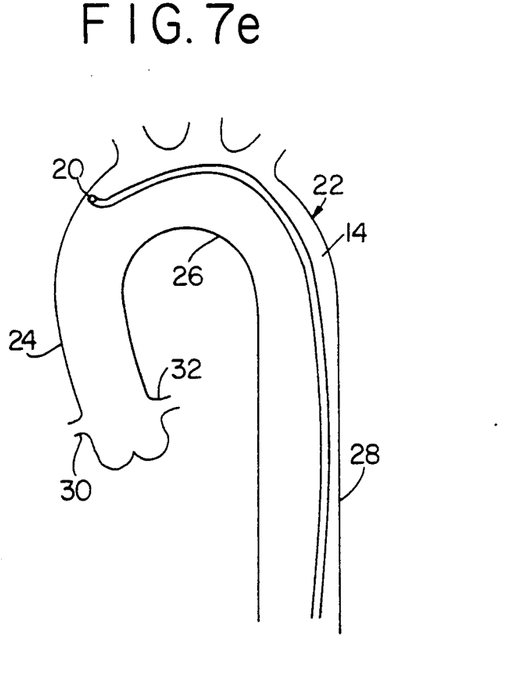
Figure 7F:
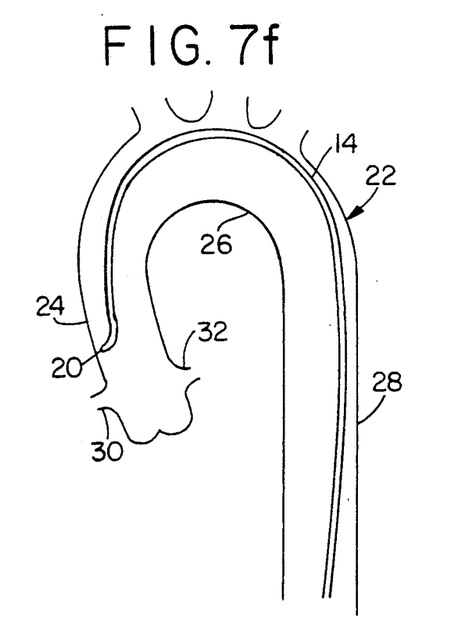
Figure 7G:
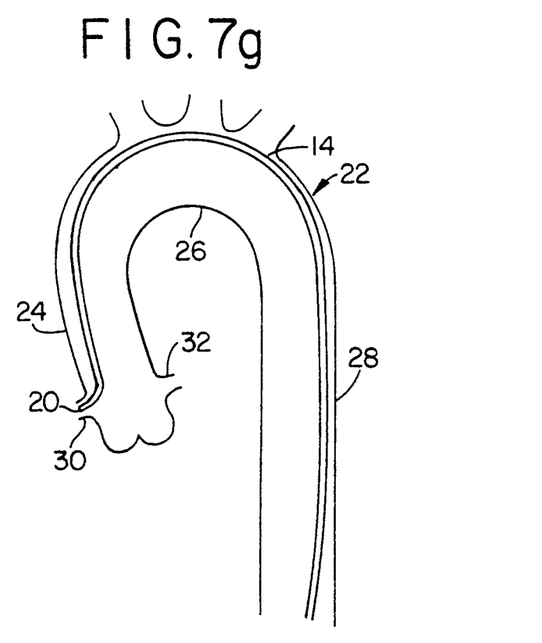

The operation of the catheter 10 of the present invention when the tip is over rotated in a clockwise position is best depicted in FIGS. 7a-g. FIG. 7a shows the catheter mis-inserted into the aorta in position which is approximately a half-clockwise turn relative to the position of the catheter 10 shown in FIG. 6a. As shown in FIG. 7b, the catheter 10 in the present invention is advanced upwardly, through the descending aorta 28 and into the vicinity of the aortic arch 26. As the catheter approaches the aortic arch 26, the tip end portion 20 generally is pointing away from the outer wall of the aorta 26, and a more proximal portion of the distal end 14 rests generally against the outer wall of the aorta 22 (as best seen in FIG. 7b). As the catheter moves upwardly, the shape of the distal end 14 of the catheter cooperates with the walls of the aorta to begin to turn the distal end in a clockwise direction (as viewed from the proximal portion) as the tip end 20 moves over the aortic arch toward the ascending aorta (see FIG. 7c). The clockwise turn of the mis-aligned catheter is greater than the degree of rotation of a catheter which is correctly inserted, because the mis-aligned catheter will rotate an additional partial turn to reach the same position it would have been in if it were inserted correctly. As the tip end 20 of the catheter moves over the aortic arch 26, the tip end 20 of the catheter cooperates with the outer wall of the aortic arch 22 and the more proximal portion of the distal portion 14 bends over the aortic arch 26 (FIG. 7d). As the tip end 20 portion moves downwardly into the ascending aorta 24, the more proximal portion of the distal end 14 contacts the outer wall of the descending aorta 24 and bends over the aortic arch 26, continuing to turn the tip end portion 20 toward a position for automatic insertion into the right coronary ostium 30 (FIG. 7e). FIG. 7f shows a more advanced position of the catheter 10. At this position, the portion of the catheter 10 generally between points 2 and 4 places an upward spring pressure on the tip end portion 20 as it advances toward the right coronary ostium 30. The portion of the catheter 10 substantially between points 5 and 8 comprises a back bend which extends over the aortic arch 26 as the tip end 20 portion 20 advances into the proximity of the right coronary ostium 30. As the catheter 10 is advanced further (FIG. 7g), the tip end portion continues to move downwardly, rotating slightly clockwise to a position ready for direct entry into the ostium when it is reached. Upon reaching the ostium, the spring pressure exerted by the portion between points 2 and 4 automatically inserts the tip end portion into the right coronary ostium 30 with little adjusting required.

Although one technique for inserting the catheter is described above, the catheter of the present invention may also be inserted over a guide wire into the vicinity of the aortic arch. For example, the catheter may be inserted until the tip end portion is just beyond the left-most ostium (as viewed in FIG. 6) of the three upper arterial branches which exit from the top of the aortic arch. The guidewire is then withdrawn and the catheter tip assumes the three dimensional shape described above. Upon further advancement of the catheter, this shape cooperates with the aortic arch to properly position the tip end portion for entry into the right coronary ostium.

It will be apparent to one skilled in the art that variations could be made within the scope of the present invention. For example, the catheter could be made of any suitable material. In addition, catheters of different size incorporating the same basic shape could be made within the scope of the present invention. These variation are merely illustrative. While the present invention is subject to variations, it is intended that all matter contained in the foregoing description or shown in the accompanying drawings shall be interpreted as illustrative and not in a limiting sense.

What is claimed is:

1. A method of performing diagnosis or treatment of the right coronary artery of a patient comprising:
   providing a catheter having an elongated hollow body with a proximal end portion and a distal end portion which is substantially curved in three dimensions;
   advancing the distal end portion through the descending aorta, over the aortic arch, into the ascending aorta, and into proximity with the ostium of the right coronary artery;
   rotating said distal end portion of said catheter as it advances over the aortic arch so as to place said tip end portion in proximity with the right coronary ostium, said rotating being the automatic result of interaction between the particular shape of the coronary catheter and the wall of the aorta, whereby the tip end portion may be placed into said ostium with minimum manual adjustment required.

2. A method in accordance with claim 1 wherein said distal end portion comprises a generally spiral shape.

3. A method in accordance with claim 1 wherein said distal end portion, when viewed from a lateral direction, comprises a most distal end portion which is arcuate and lies substantially within a first plane and a more proximal portion which is arcuate and lies substantially within a second plane, said second plane being disposed at an angle to said first plane.

4. A method in accordance with claim 3 wherein said distal end portion includes an arcuate portion not lying in either plane and extending between said most distal end portion and said other portion.

5. A method in accordance with claim 1 wherein said distal end portion comprises a plurality of curves of increasingly smaller radii in the direction of said tip end portion.

6. A method in accordance with claim 5 wherein said distal end portion comprises at least three areas of increasingly smaller radii, each lying in three different planes.

7. A method in accordance with claim 5 wherein said distal end portion includes a portion between said tip end portion and a more proximal curved portion which is disposed to deform and thereby place a spring-like pressure on said tip end portion as said tip end portion is advanced toward the right coronary ostium.

8. A method in accordance with claim 1 in which said shape cooperates with the aorta to rotate such distal end portion as said distal end portion advances over the aortic arch and into proximity with the right coronary ostium.

* * * * *